United States Patent [19]

Thoemel et al.

[11] 4,426,332
[45] Jan. 17, 1984

[54] PREPARATION OF RESORCINOL DERIVATIVES

[75] Inventors: Frank Thoemel, Weinheim; Werner Hoffmann, Neuhofen, both of Fed. Rep. of Germany

[73] Assignee: BASF Aktiengesellschaft, Ludwigshafen, Fed. Rep. of Germany

[21] Appl. No.: 370,404

[22] Filed: Apr. 21, 1982

[30] Foreign Application Priority Data

Apr. 29, 1981 [DE] Fed. Rep. of Germany ....... 3116913

[51] Int. Cl.³ .................. C07C 121/75; C07C 37/00; C07C 41/00; C07C 69/84
[52] U.S. Cl. ................... 260/465 F; 560/64; 560/70; 568/648; 568/650; 568/771
[58] Field of Search ............... 260/465 F; 560/64, 70; 568/648, 650, 771

[56] References Cited

U.S. PATENT DOCUMENTS 3,819,725 6/1974 Brossi et al. .................. 568/648 X
3,859,365 1/1975 Young .............................. 568/626
4,072,660 2/1978 Muller et al. ................. 568/650 X Primary Examiner—Dolph H. Torrence Attorney, Agent, or Firm—Oblon, Fisher, Spivak, McClelland & Maier

[57] ABSTRACT

A process for the preparation of resorcinol derivatives of the general formula I

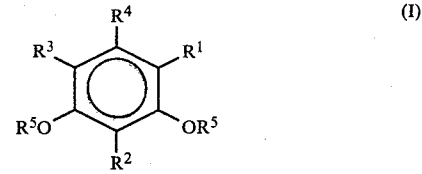

where $R^1$ is carbalkoxy, nitrile, alkyl or H and $R^2$ to $R^5$ are H or lower alkyl, by reacting the corresponding cyclohexane-1,3-dione (II) with oxygen or an oxygen-containing gas in the presence of a catalytic amount of a copper compound and of from 1 to 10 moles of a hydrogen halide, or from 0.5 to 5 moles of thionyl chloride per mole of II, in an alkanol having from 1 to 6 carbon atoms, tetrahydrofuran or methyl tert.-butyl ether as the solvent, at from 0° to 150 C., without the addition of a significant amount of water to the reaction mixture. Some of the resorcinol derivatives prepared are useful scents with fragrance notes of the character of the odoriferous substance of natural oak moss.

8 Claims, No Drawings

PREPARATION OF RESORCINOL DERIVATIVES

The present invention relates to a process for the preparation of resorcinol derivatives of the general formula I

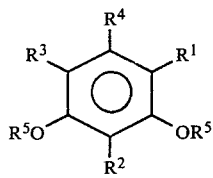

where $R^1$ is lower carbalkoxy, nitrile, lower alkyl or hydrogen and $R^2$ to $R^5$ are hydrogen or lower alkyl, and to the use of resorcinol derivatives of the general formula III

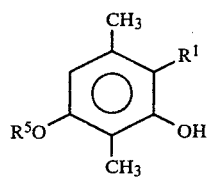

where $R^1$ is lower carbalkoxy or nitrile and $R^5$ is lower alkyl, as scents in perfume compositions.

Oak moss extracts are important in perfumery, chiefly in the production of chypre or fougère compositions. The most important odoriferous substances of natural oak moss include β-resorcylic acid derivatives, and attempts are ever being made to obtain such compounds, either from the naturally occurring constituents of oak moss (cf. R. Ter Heide et al., Parfums, Cosmétiques, Aromes 3 (1975, 61) or as purely synthetic products.

The synthetically readily available dihydro-β-resorcylic acid derivatives of the general formula IV

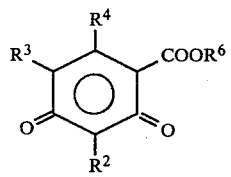

where $R^6$ is lower alkyl and $R^2$ and $R^4$ are hydrogen or lower alkyl, can be used as starting materials for synthetic β-resorcylic acid derivatives. The compounds IV can be prepared either by condensation of α,β-unsaturated carboxylic acid esters with β-keto-esters (cf. A. Sonn, Ber. Chem. Ges. 62 (2) (1929), 3012), or by condensation of malonates with α,β-unsaturated ketones (cf. U. Steiner and B. Wilhelm, Helv. Chim. Acta 35 (1952), 1752).

The main problem in the synthesis of the above oak moss scents of the resorcinol type is the aromatization of the compounds IV. A. Sonn (loc. cit.) used an expensive palladium catalyst for this purpose. German Published Application DAS No. 1,941,041 and U.S. Pat. No. 3,634,491 propose chlorine or chlorine-generating substances as oxidants. If bromine in glacial acetic acid is used (U.S. Pat. No. 3,884,843), bromine-substituted aromatics which still have to be dehalogenated are obtained. However, the use of halogens requires special equipment and presents problems of working safety and environmental safety. Aromatization with the aid of acetic anhydride/sulfuric acid is relatively simple (cf. German Laid-Open Application DOS No. 2,653,177). However, the diacetates are first formed, and these must be hydrolyzed in an additional reaction stage.

It is an object of the present invention to provide a process by which the resorcinol derivatives of the formula I can be prepared in good yield and in a simple manner, avoiding the disadvantages of the conventional processes.

We have found that this object is achieved by a process for the preparation of resorcinol derivatives of the general formula I

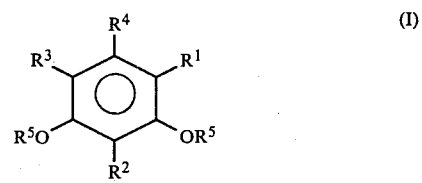

where $R^1$ is lower carbalkoxy, nitrile, lower alkyl or hydrogen and $R^2$ to $R^5$ are hydrogen or lower alkyl, wherein the corresponding cyclohexane-1,3-dione of the general formula II

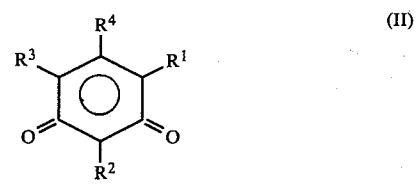

where the substituents have the above meanings, is reacted with oxygen or an oxygen-containing gas in the presence of a catalytic amount of a copper compound and in the presence of from 1 to 10 moles, preferably from 5 to 10 moles, of a hydrogen halide or of from 0.5 to 5 moles, preferably from 1 to 3 moles, of thionyl chloride per mole of II, in a substantially anhydrous alkanol of from 1 to 6 carbon atoms, substantially anhydrous tetrahydrofuran or substantially anhydrous methyl tert.-butyl ether as the solvent, at from 0° to 150° C., preferably from 20° to 100° C.

In a particularly advantageous embodiment of the process, the reaction is carried out in the presence of a catalytic amount of copper-I oxide and/or in the presence of hydrogen chloride, hydrogen bromide or thionyl chloride.

The present invention also relates to the use of resorcinol derivatives of the general formula III

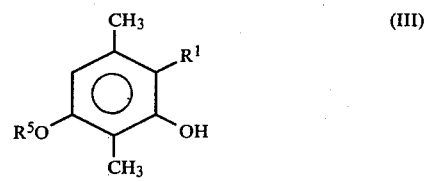

where $R^1$ is lower carbalkoxy, preferably carbomethoxy, or nitrile and $R^5$ is lower alkyl, as scents.

It is surprising that particularly good yields of the resorcinol derivatives of the formula I can be prepared by the process according to the invention.

Although U.S. Pat. No. 3,859,365 discloses that relatively good yields of alkyl-substituted phenols can be prepared by reacting the corresponding cyclohex-2-en-1-ones with oxygen at from 20° to 200° C. in the presence of copper-II chloride, hydrochloric acid and a water-miscible solvent, attempts to apply this procedure to the reaction of cyclohexane-1,3-diones result in exceptionally low yields of the resorcinol derivatives of the formula I. For example, reaction of methyl 3,6-dimethyl-$\beta$-dihydroresorcylate by the processes of the U.S. patent gives methyl 3,6-dimethyl-$\beta$-resorcylate as the sole aromatization product, in a maximum yield of 17% of theory. Surprisingly, we have now found that this reaction gives a very good yield of aromatization product if it is carried out with virtually no addition of water to the reaction mixture.

Those cyclohexane-1,3-diones of the formula II where $R^1$ is carbalkoxy of 1 to 4 carbon atoms, in particular carbomethoxy, or nitrile and $R^2$ and $R^4$ are hydrogen or alkyl of 1 to 4 carbon atoms, in particular hydrogen or methyl, are preferably used as the starting compounds.

Suitable catalysts include organic or inorganic copper-I salts and copper-II salts, and copper-I oxide and copper-II oxide. The copper salts may also contain water of crystallization. Examples of catalysts are CuCl, $CuCl_2 \times 2H_2O$, $CuBr_2$, $Cu(CH_3CO)_2$, $Cu_2O$, CuO and $Cu(NO_3)_2$, and $Cu_2O$ is particularly advantageous. From 0.01 to 0.5 mole, preferably from 0.05 to 0.3 mole, of catalyst per mole of II is generally employed.

According to the invention, hydrogen chloride gas or hydrogen bromide gas is advantageously used as the hydrogen halide, but thionyl chloride can also be employed. Not less than one mole of hydrogen halide or thionyl chloride is generally used per mole of cyclohexanedione II, and the advantageous amount is from 5 to 10 moles of hydrogen halide or from 1 to 3 moles of thionyl chloride per mole of II.

Lower alkanols, such as methanol, ethanol, propanol, butanol, amyl alcohol, isopropyl alcohol and tert.-butyl alcohol, or methyl tert.-butyl ether are used as the solvent in the processes according to the invention. Tetrahydrofuran has also proved suitable for the preparation of resorcinol derivatives containing non-etherified hydroxyl groups. Not less than the amount of solvent required for dissolving the compound to be aromatized must be used. Dimethylformamide, aromatic or aliphatic hydrocarbons and halohydrocarbons are very unsuitable or even totally unsuitable.

Virtually anhydrous solvents, ie. solvents which contain no significant amounts of water, are used according to the invention, and care is taken that no noticeable amounts of water are added to the reaction mixture. As comparative experiments show, even about 5% of added water in the solvent results in considerable losses in yield. Any water which may be introduced in the form of water of crystallization in the copper salt catalyst, and the water formed during the reaction, do not substantially impede the reaction.

The reaction according to the invention is generally carried out under atmospheric pressure at from below the boiling point to no higher than the boiling point of the solvent used, usually at from 20° to 100° C. In principle, however, the reaction can also be carried out in a pressure vessel, air or oxygen being forced in.

From 10 to 2,000 liters per hour, but preferably from 40 to 1,000 liters per hour, of air or oxygen are required for oxidation of one mole of substrate. As a rule, the air or oxygen is passed into the reaction mixture, but it is also possible to add a solution of the starting compound dropwise to a solution of the catalyst system and, in doing so, at the same time to introduce air or oxygen into the reaction mixture.

The reaction time can be from a few hours to some days, depending on the reaction conditions chosen. Advantageously, these conditions are chosen so that the aromatization process has ended after not more than 15 hours.

In most cases, a crystalline precipitate is obtained in the reaction and is directly filtered off with suction and can be recrystallized from a suitable solvent, e.g. ethanol/water. The mother liquor is then concentrated and worked up by distillation to isolate the residual amounts of I.

If an alkanol is used as the solvent, the main products formed can be a resorcinol derivative Ia, its monoether Ib or its bis-ether Ic.

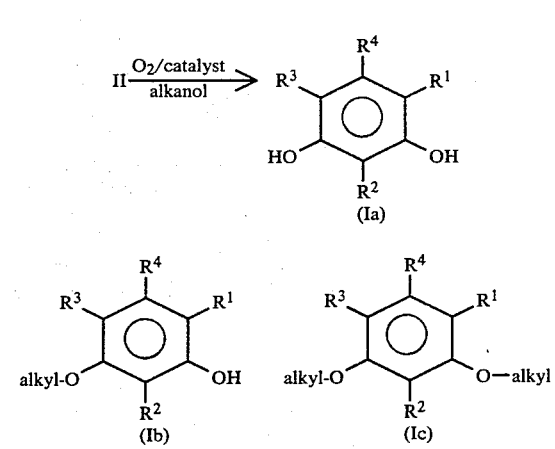

The yield and the proportions of the various products Ia–c formed in the process according to the invention chiefly depend on the substituents $R^1$ and $R^4$ in formula I and on the alkanol used as the solvent.

3,6-Dialkyl-$\beta$-dihydroresorcylates and the corresponding nitriles (general formula II where $R^1$ is alkoxycarbonyl or nitrile, $R^2$ and $R^4$ are alkyl and $R^3$ is hydrogen) can particularly advantageously be aromatized by the process according to the invention, preferably using copper compounds in combination with hydrogen chloride or thionyl chloride as the catalyst system and methanol as the solvent. Methyl 3,6-dimethyl-$\beta$-dihydroresorcylate then gives, as the aromatization product, a maximum yield of over 80% of theory of methyl rhizoninate VI of type Ib, in addition to about 10% of methyl 3,6-dimethyl-$\beta$-resorcylate VII of type Ia.

VI

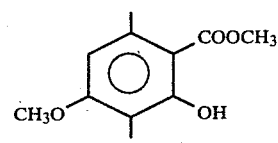

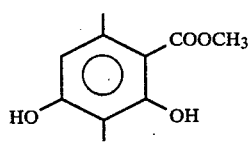

VII

In contrast cyclohexane-1,3-dione ($R^2$ to $R^4$ are H), for example, can be converted in 76% yield, to 1,3-dimethoxybenzene of type Ic over a $Cu_2O$/thionyl chloride catalyst in methanolic solution. A 60% yield of 1,3-dimethoxy-5-methyl-benzene is obtained as the main product from 5-methyl-cyclohexane-1,3-dione under the same conditions.

If isopropanol or tert.-butanol is used as the solvent instead of methanol in the reaction of 3,6-dialkyl-β-dihydroresorcylates, a larger amount of the 3,6-dimethyl-β-resorcylate with non-etherified hydroxyl groups (VII) is formed, and in extreme cases this can even become the main product.

Products of the type of the general formula Ib where the ether and ester radicals are identical or different are obtained, in addition to the compound VII, in the presence of lower primary and secondary alcohols. Compounds of the type Ib where alkyl is methyl are preferentially formed in the presence of methyl tert.-butyl ether.

If resorcinol derivatives with non-etherified hydroxyl groups are to be prepared exclusively, it is advisable to carry out the reaction in tetrahydrofuran as the solvent.

Methyl-3,6-dimethyl-β-resorcylate VII, as a content of natural oak moss, is an important commercial product for perfumery. We have found that the quality and intensity odor of the monomethyl ether VI are comparable to those of this product, and also that the corresponding nitrile is a good scent with an oak moss character.

The process according to the invention thus offers the possibility of preparing, not only the desirable odoriferous substances of natural oak moss, but also good yields of resorcinol derivatives with comparably good scent properties and, in addition, of resorcinol derivatives of the general formulae Ia–Ic in a simple manner.

EXAMPLE 1

11.9 g (0.1 mole) of thionyl chloride and 1 g (7 mmoles) of copper-I oxide are added to a solution of 9.9 g (50 mmoles) of methyl 3,6-dimethyl-β-dihydroresorcylate in 100 ml of methanol. A stream of 45 liters/hour of air is passed into this reaction mixture at 50° C., with stirring, for 6 hours. The reaction mixture is then concentrated to one third of its volume and is left to stand overnight at from 0° to 5° C. The crystalline precipitate is then collected on a Büchner funnel, washed with cold methanol and dried to give 7.63 g of methyl 3,6-dimethyl-2-hydroxy-4-methoxy-benzoate VI (methyl rhizoninate) of melting point 87°–90° C.

The mother liquor is freed from solvent and the residue is distilled. 2.61 g of a product mixture which, according to analysis by gas chromatography (2 m OV-17; 200° C.), consists of 20.4% of methyl 3,6-dimethyl-β-resorcylate VII and 46.8% of methyl rhizoninate VI pass over at 100°–120° C./0.1 mbar. The total yield of methyl resorcinate VI is 8.85 g (42 mmoles)=84% of theory, and that of methyl 3,6-dimethyl-β-resorcylate VII is 0.53 g (3 mmoles)=6% of theory.

1 H-NMR spectrum (CDCl$_3$) of methyl rhizoninate: δ=2.08 (s, —CH$_3$), 2.50 (s, —CH$_3$), 3.85 (s, —CH$_3$), 3.90 (s, —CH$_3$), 6.25 (s. H) and 11.75 ppm (OH).

Fragrance note of methyl rhizoninate: oak moss; comparable to that of VII.

EXAMPLE 2

250 g of hydrogen chloride gas are passed into 3 l of methanol at room temperature, 198 g (1 mole) of methyl 3,6-dimethyl-β-dihydroresorcylate are dissolved in the resulting HCl/methanol mixture, and 20 g (0.14 mole) of Cu$_2$O are added. A stream of 75 l/hour of air is passed into this reaction mixture at 50° C., with stirring, for 11 hours. The reaction product is worked up by a method similar to that in Example 1 to give a total of 166.6 g (0.79 mole), corresponding to 79% of theory, of methyl rhizoninate VI, 150 g of which are obtained in the form of pure crystals, and 26.1 g (0.13 mole), corresponding to 13% of theory, of methyl 3,6-dimethyl-β-resorcylate VII.

EXAMPLES 3–10

Methyl 3,6-dimethyl-β-dihydroresorcylate (IIa) is oxidized under various conditions by a method similar to that in Examples 1 and 2. More details of the starting compound, reaction conditions and yields of methyl rhizoninate (VI) and of methyl 3,6-dimethyl-β-resorcylate (VII) can be found in Table 1 which follows. Example 4 is carried out with pure oxygen.

TABLE 1

| Example | 3 | 4 | 5 | 6 | 7 | 8 | 9 | 10 |
|---|---|---|---|---|---|---|---|---|
| Starting compound (IIa) [moles] | 0.05 | 0.05 | 0.05 | 0.05 | 0.05 | 0.05 | 0.05 | 0.05 |
| Catalyst | Cu$_2$O | Cu$_2$O | CuCl | CuCl$_2$ × 2H$_2$O | CuBr$_2$ | CuAc$_2$ | Cu$_2$O | Cu$_2$O |
| Amount [mmoles] | 7 | 7 | 10 | 6 | 4.5 | 5.5 | 7 | 7 |
| Auxiliary reagent | HCl | HCl | HCl | HCl | HCl | HCl | HBr | SOCl$_2$ |
| Amount [g] | 12 | 13 | 12 | 12 | 16 | 11 | 8 | 12 |
| Solvent | MeOH | MeOH | MeOH | MeOH | MeOH | MeOH | MeOH | +0− |
| Amount [ml] | 100 | 100 | 100 | 100 | 100 | 100 | 100 | 100 |
| Stream of air (or O$_2$ at+) [liters/hour] | 10 | 10+ | 45 | 45 | 45 | 45 | 45 | 45 |
| Reaction temperature [°C.] | 50 | 50 | 50 | 50 | 50 | 50 | 50 | 50 |
| Reaction time [hours] | 12 | 5 | 7 | 5 | 4 | 11 | 13 | 4.5 |
| Yield of VI [% of theory] | 81.2 | 67.6 | 77.5 | 52.8 | 66.6 | 51.0 | 64,0 | 76.9 |
| Yield of VII [% of theory] | 10.0 | 8.1 | 9.3 | 8.4 | 15.2 | 8.5 | 2.7 | 12.6 |

EXAMPLE 11

9.9 g (0.05 mole) of methyl 3,6-dimethyl-β-dihydroresorcylate are reacted by a method similar to that in Example 2, in the presence of 1 g (6 mmoles) of CuCl$_2$.2H$_2$O and 12 g of hydrogen chloride in solution in 100 ml of n-amyl alcohol. Reaction temperature: 50° C.; stream of air: 40 liters/hour; reaction time: 6 hours; yield of VII: 18% of theory; yield of methyl 3,6-dimethyl-2-hydroxy-4-amyloxy-benzoate, of melting point 67°–68° C.: 72.5% of theory; 1 H-NMR spectrum (CDCl$_3$): δ = 1.05 (+, —CH$_3$), 1,1–2 (m—CH$_2$), 2.04 (s, —CH$_3$), 2.46 (s, —CH$_3$), 3.82 (s, —CH$_3$), 3.9 (+, —CH$_2$), 6.12 (s, H) and 11.47 ppm (s, OH).

EXAMPLE 12

9.9 g (0.05 mole) of methyl 3,6-dimethyl-β-dihydroresorcylate are reacted by a method similar to that in Example 2 in the presence of 1 g (7 mmoles) of Cu$_2$O and 15 g of hydrogen chloride in solution in 100 ml of isopropanol. Reaction temperature: 50° C.; stream of air: 45 liters/hour; reaction time: 8 hours; yield of VII: 38.1% of theory; yield of methyl 3,6-dimethyl-2-hydroxy-4-isopropoxy-benzoate of melting point 78°–80° C.: 48.5% of theory; 1 H-NMR spectrum (CDCl$_3$): δ = 1.30 (d, 2—CH$_2$), 2.01 (s, —CH$_3$, 2.42 (s, —CH$_3$), 3.80 (s, —CH$_3$), 4.48 (m), 6.12 (s, —H) and 11.66 ppm (s, OH).

EXAMPLE 13

8.3 g (0.05 mole) of 3,6-dimethyl-2,4-dioxocyclohexanonitrile are reacted in the presence of 1 g (7 mmoles) of Cu$_2$O and 15 g of hydrogen chloride gas in solution in 100 ml of methanol. Reaction temperature: 50° C.; stream of air: 45 liters/hour; reaction time: 9 hours; yield of 3,6-dimethyl-2,4-dihydroxy-benzonitrile: 14.7% of theory; yield of 3,6-dimethyl-2-hydroxy-4-methoxy-benzonitrile of melting point 155°–157° C.: 58.6% of theory; 1 H—NMR spectrum (CdCl$_3$): δ = 2.0 (s, —CH$_3$), 2.36 (s, —CH$_3$), 3.81 (s, —CH$_3$), 6.56 (s, —H) and 9.72 ppm (s, —OH).

EXAMPLE 14

17 g (0.1 mole) of methyl β-dihydroresorcylate are reacted by a method similar to that in Example 1 in the presence of 2 g (14 mmoles) of Cu$_2$O and 24 g (0.2 mole) of thionyl chloride in solution in 200 ml of methanol. Reaction temperature: 50° C.; stream of air: 45 liters/hour; reaction time: 13 hours; yield of 1,3-dimethoxy-benzene: 7% of theory; yield of methyl 2-hydroxy-4-methoxy-benzoate of melting point 47°–48° C.: 21% of theory; 1 H-NMR spectrum (CDCl$_3$): 2.51 (s, —CH$_3$), 3.90 (s. —CH$_3$), 3.95 (s, —CH$_3$), 6.30 (s, 2H) and 12.2 ppm (s, OH); yield of methyl 2,4-dimethoxy-benzoate: 27.9% of theory; 1 H—NMR spectrum (CDCl$_3$): δ = 3.80 (s, —CH$_3$), 3.82 (s, —CH$_3$), 3.86 (s, —CH$_3$), 6.45 (m, 2H) and 7.78 ppm (m, H); n$_D^{25}$ = 1.5432.

EXAMPLE 15

11.2 g (0.1 mole) of cyclohexane-1,3-dione are reacted by a method similar to that in Example 1 in the presence of 2 g (14 mmoles) of Cu$_2$O and 24 g (0.2 mole) of thionyl chloride in solution in 200 ml of methanol. Reaction temperature: 50° C.; stream of air: 45 liters/hour; reaction time: 10 hours; yield of 1,3-dimethoxy-benzene: 76% of theory, 1 H-NMR spectrum (CDCl$_3$) = 3.78 (s, 2—CH$_3$), 6.49 (m, 3H) and 7.18 ppm (m, 1H).

EXAMPLE 16

6.3 g (0.05 mole) of 5-methyl-cyclohexane-1,3-dione are reacted by a method similar to that in Example 1 in the presence of 1 g (7 mmoles) of Cu$_2$O and 12 g (0.1 mole) of thionyl chloride in solution in 100 ml of methanol. Reaction temperature: 50° C.; stream of air: 45 liters/hour; reaction time: 8 hours; yield of 1,3-dimethoxy-5-methyl-benzene: 60% of theory; mass spectrum (70 eV).

EXAMPLE 17

25 g of hydrogen chloride gas are passed into 200 ml of tetrahydrofuran (TMF (sic)) at 25° C. 2 g of Cu$_2$O and 19.8 g of methyl 3,6-dimethyl-β-dihydro-resorcylate are added to this solution. The reaction mixture is then heated to 50° C. and a stream of 45 liters/hour of air is passed in. After 7 hours, all the starting material has reacted.

The reaction mixture is concentrated and the concentrate is poured on to a water/toluene mixture, the organic phase is separated off, washed neutral with water and concentrated, and, finally, the residue is distilled over a bridge. A yield of 53.8% of theory of methyl 3,6-dimethyl-β-resorcylate VII is obtained.

EXAMPLE 18

(a) Under conditions according to the invention 12 g of hydrogen chloride gas are passed into 100 ml of methanol at room temperature, 9.9 g (0.05 mole) of methyl 3,6-dimethyldihydro-β-resorcylate are dissolved in the resulting HCl/methanol mixture and 1 g (7 mmoles) of Cu$_2$O is added.

A stream of 45 liters/hour of air is passed into this reaction mixture at 50° C. until, according to analysis by thin layer chromatography, all the starting compound has reacted.

The reaction mixture is concentrated to ⅓ of its volume and is cooled to 5° C., and the crystals which precipitate are separated off. The mother liquor is poured into a water/toluene mixture, the organic phase is separated off, washed neutral with water and concentrated, and, finally, the residue is distilled over a bridge.

A total yield of 81% of theory of methyl rhizoninate (VI) and a total yield of 10% of theory of methyl 3,6-dimethyl-β-resorcylate (VII) are obtained.

(b) Comparative example with the addition of 5 ml of water to the reaction mixture The procedure followed is as described under (a), but instead of 100 ml of methanol, a mixture of 100 ml of methanol and 5 ml of water is used. A total yield of 34.9% of theory of methyl rhizoninate (VI) and a total yield of 18% of methyl 3,6-dimethyl-β-resorcylate (VII) are obtained.

(c) Comparative example with the addition of 10 ml of water to the reaction mixture The procedure followed is as described under (a), but instead of 100 ml of methanol, a mixture of 100 ml of methanol and 10 ml of water is used as the solvent. A total yield of only 34.3% of theory of methyl rhizoninate and a yield of 15.9% of theory of methyl 3,6-dimethyl-β-resorcylate (VII) are obtained.

We claim:

1. A process for the preparation of a resorcinol derivative of the formula I

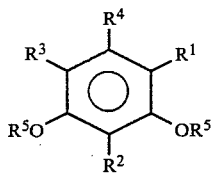

where $R^1$ is lower carbalkoxy, nitrile, lower alkyl or hydrogen and $R^2$ to $R^5$ are hydrogen or lower alkyl, wherein the corresponding cyclohexane-1,3-dione of the formula II

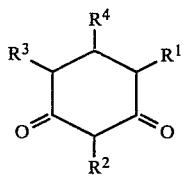

where the substituents have the above meanings, is reacted with oxygen or an oxygen-containing gas in the presence of a catalytic amount of a copper compound and in the presence of from 1 to 10 moles of a hydrogen halide, or of from 0.5 to 5 moles of thionyl chloride, per mole of II, in a substantially anhydrous alkanol of from 1 to 6 carbon atoms, substantially anhydrous tetrahydrofuran or substantially anhydrous methyl tert.-butyl ether as the solvent, at from 0° to 150° C.

2. A process for the preparation of a resorcinol derivative of the formula I as claimed in claim 1, wherein the reaction is carried out in the presence of a catalytic amount of copper-I oxide.

3. A process for the preparation of a resorcinol derivative of the formula I as claimed in claim 1, wherein the reaction is carried out in the presence of hydrogen chloride, hydrogen bromide or thionyl chloride.

4. A process for the preparation of a resorcinol derivative of the formula I as claimed in claim 1, wherein the reaction is carried out at from 20° to 100° C.

5. The process of claim 1, wherein $R^1$ is lower carbalkoxy or nitrile.

6. The process of claim 2, wherein $R^1$ is lower carbalkoxy or nitrile.

7. The process of claim 3, wherein $R^1$ is lower carbalkoxy or nitrile.

8. The process of claim 4, wherein $R^1$ is lower carbalkoxy or nitrile.

* * * * *